United States Patent [19]

Moretz et al.

[11] Patent Number: 5,414,870
[45] Date of Patent: May 16, 1995

[54] MOISTURE MANAGEMENT COMPONENT AND GARMENTS INCORPORATING A MOISTURE MANAGEMENT COMPONENT

[75] Inventors: Herbert L. Moretz, Davidson, N.C.; Daniel L. Brier, Key Largo, Fla.

[73] Assignee: Intelpro Corporation, Lincolnton, N.C.

[21] Appl. No.: 78,413

[22] Filed: Jun. 17, 1993

Related U.S. Application Data

[63] Continuation-in-part of Ser. No. 47,841, Apr. 15, 1993.

[51] Int. Cl.⁶ .................................................. A41B 9/00
[52] U.S. Cl. ............................................ 2/400; 2/402; 2/403; 2/406; 2/409; 604/378; 604/393
[58] Field of Search .................... 2/400, 402, 403, 406, 2/409, 238; 604/378, 393

[56] References Cited

U.S. PATENT DOCUMENTS

| | | |
|---|---|---|
| 549,048 | 10/1895 | Basch . |
| 3,237,625 | 3/1966 | Johnson . |
| 3,613,687 | 10/1971 | Kennedy . |
| 3,882,871 | 5/1975 | Taniguchi . |
| 4,555,245 | 11/1985 | Armsruster . |
| 4,880,424 | 11/1989 | Rautenberg . |
| 4,916,005 | 4/1990 | Lippert . |
| 4,961,419 | 10/1990 | Tribble . |
| 5,037,409 | 8/1991 | Chen et al. . |
| 5,152,014 | 10/1992 | Marx et al. . |
| 5,210,882 | 5/1993 | Moretz et al. . |
| 5,217,782 | 6/1993 | Moretz et al. . |

FOREIGN PATENT DOCUMENTS

| | | |
|---|---|---|
| 0202125 | 5/1986 | European Pat. Off. . |
| 2176692A | 6/1985 | United Kingdom . |

OTHER PUBLICATIONS

CA Hydrofil Nylon, Jul. 1988. By Allied Signal.

Primary Examiner—Andrew M. Falik
Assistant Examiner—Gloria Hale
Attorney, Agent, or Firm—W. Thad Adams, III

[57] ABSTRACT

A moisture management component incorporated in a garment for moving moisture away from the skin of a wearer. The moisture management component includes a first and second fabric. The first fabric comprises a moisture wicking panel carried by the garment for moving moisture away from the skin. The moisture wicking panel has a skin-side surface and an obverse surface, and an opening therethrough from the skin-side surface to the obverse surface. The second fabric comprises a moisture transport insert extending through the opening in the moisture wicking panel to move moisture from the skin of the wearer to the outer fabric layers of the garment for dispersal and evaporation.

24 Claims, 9 Drawing Sheets

5,414,870

MOISTURE MANAGEMENT COMPONENT AND GARMENTS INCORPORATING A MOISTURE MANAGEMENT COMPONENT

This application is a continuation-in-part of U.S. Ser. No. 08/047,841, filed on Apr. 15, 1993.

TECHNICAL FIELD AND BACKGROUND OF THE INVENTION

This invention relates to a moisture management component and garments incorporating a moisture management component. The moisture management component is located generally in the crotch area of the garment, and is designed to move moisture in a direct path from the skin of the wearer to the outer fabric layers of the garment, away from the skin. The moisture management component does not absorb moisture and hold moisture against the skin to prevent leakage from the garment, as in many prior art garments. Instead, moisture is quickly transported away from the skin along the fibers of the moisture management component to drier areas of the garment where evaporation occurs.

The invention has particular application in undergarments for controlling leakage and spotting caused by minor to moderate urinary incontinence and in colostomy patients. Additionally, the invention has application in many types of athletic apparel where perspiration-soaked garments next to the skin over a period of time can cause chafing, irritation and conditions conducive to bacteria, fungus and yeast growth.

The garments incorporating the moisture management component are specifically intended to be indistinguishable in outer appearance from similar garments without such a component. For this reason, the invention uses combinations of fibers which are intended to quickly remove moisture from the area of the skin and disperse the moisture into areas away from the skin in relatively thin layers over a relatively large surface area. Many disposable urinary incontinence products, concentrate the moisture away from the skin in a relatively small, bulky area. Thus, these type garments require frequent changing, and do not promote the evaporation of moisture.

The fabric of the moisture management component permits minor to moderate amounts of liquid to be dispersed without penetrating the garment's outer layer, thus preventing spotting or staining of the garment or of other garments worn over the garment. Thus, one object of the invention is to permit the control of relatively small amounts of moisture, but over a long period of time, such as most or all of a day. Garments incorporating the novel moisture management component are permitted to look and fit essentially like conventional garments of otherwise conventional construction. This avoids embarrassment to the wearer and encourages use. The availability of such a garment will permit the wearer to avoid use of bulky disposable garments, and will promote self-esteem.

The novel garment incorporating the moisture management component can be worn over an extended period of time, and is specifically intended to receive and properly manage multiple instances of minor wetting without having to change the garment. This is virtually essential if the garment is going to be used by active wearers, particularly those in the business or work environment where storage and use of bulky diaper-like products is difficult if not impossible to accomplish without embarrassment.

Additionally, garments incorporating the present invention can be laundered and worn repeatedly, exactly as other conventional garments. Although the garment may be more expensive than similar styles of garments of conventional construction, the ability to repeatedly launder and wear the garment makes it far less expensive than disposable products.

SUMMARY OF THE INVENTION

Therefore, it is an object of the invention to provide a moisture management component for incorporation in a garment to effectively manage moisture resulting from heavy perspiration or mild incontinence.

It is another object of the invention to provide a moisture management component which is located in the crotch area of a garment such as a man's brief, boxer-type undershorts, a woman's panty, panty hose, or a diaper to move moisture from this area and away from the skin of the wearer.

It is another object of the invention to provide a moisture management component which moves moisture both outwardly away from the skin of the wearer, and upwardly towards the waist area of the garment for enhanced evaporation.

It is another object of the invention to provide a moisture management component which moves moisture directly from the inner layers of the garment near the skin to the outer layers of the garment away from the skin.

It is another object of the invention to provide a relatively inexpensive moisture management garment which can be laundered and reused as often as desired.

It is another object of the invention to provide a garment incorporating a moisture management component that is essentially indistinguishable from garments of a conventional construction.

It is another object of the invention to provide a garment incorporating a moisture management component which can be comfortably worn over an extended period of time, such as all day.

These and other objects of the present invention are achieved in the preferred embodiments disclosed below by providing a moisture management component in a garment for moving moisture away from the skin of a wearer. The moisture management component includes a first and second fabric. The first fabric comprises a moisture wicking panel carried by the garment for moving moisture away from the skin. The moisture wicking panel has a skin-side surface and an obverse surface, and an opening therethrough from the skin-side surface to the obverse surface.

The second fabric comprises a moisture transport insert extending through the opening in the moisture wicking panel. The moisture transport insert has a first and second portion. The first portion is positioned in overlying relation on the skin-side surface of the moisture wicking panel for receiving moisture from the skin and from the moisture wicking panel. The second portion is positioned in overlying relation on the obverse surface of the moisture wicking panel for receiving moisture from the first portion of the moisture transport insert through the opening and to the obverse face of the moisture wicking panel for dispersal.

According to one preferred embodiment of the invention, the first portion of the moisture transport insert resides generally in a lower crotch area of the garment and is relatively narrow with a relatively small surface area. The second portion of the moisture transport insert resides generally in an upper crotch area of the garment and is relatively wide with a relatively large surface area. The second portion provides greater moisture absorption capacity in the upper crotch area of the garment to promote the transport of moisture upwardly towards a drier area of the garment where moisture can more easily be dispersed.

Preferably, the width of the moisture transport insert tapers from the relatively wide second portion towards the relatively narrow first portion.

According to another preferred embodiment of the invention, the moisture wicking panel defines a second opening therethrough located in spaced-apart relation to the first opening for inserting a free end of the relatively narrow first portion of the moisture transport insert through the moisture wicking panel from the skin-side surface of the moisture wicking panel to the obverse surface of the moisture wicking panel.

According to one preferred embodiment of the invention, the moisture wicking panel comprises a fabric constructed of moisture wicking fibers having a high surface area in relation to volume.

According to another preferred embodiment of the invention, the moisture wicking panel comprises an integrally knit bi-component fabric constructed of moisture wicking fibers on an inner fabric face thereof for residing nearest the skin of the wearer, and hydrophilic fibers on an obverse fabric face thereof for residing away from the skin of the wearer.

According to one preferred embodiment of the invention, the moisture transport insert comprises a fabric constructed substantially of moisture wicking fibers having a high surface area in relation to volume.

According to another preferred embodiment of the invention, the moisture transport insert comprises an integrally knit bi-component fabric constructed of hydrophilic fibers on an inner fabric face thereof for residing nearest the skin of the wearer, and moisture wicking fibers on an obverse fabric face thereof for residing away from the skin of the wearer.

According to yet another preferred embodiment of the invention, the moisture transport insert comprises a fabric chemically treated for speeding the movement of moisture along the fibers of the moisture transport insert.

Preferably, the moisture transport insert is attached to the moisture wicking panel by sew stitching a portion of the moisture transport insert to the moisture wicking panel.

Preferably, the moisture management component includes a fabric comfort liner constructed of moisture wicking fibers for residing between the moisture wicking panel and the skin of the wearer to wick moisture away from the skin of the wearer.

According to one preferred embodiment of the invention, the fabric comfort liner comprises an integrally knit bi-component fabric constructed of moisture wicking fibers on an inner fabric face thereof for residing nearest the skin of the wearer, and hydrophilic fibers on an obverse fabric face thereof for residing away from the skin of the wearer.

Preferably, the moisture management component further includes a liquid impermeable, vapor permeable microfiber fabric layer comprising a microfiber shield for providing a leak-proof barrier which prevents passage of liquid but permits dissipation of moisture in vapor form through the fabric.

Preferably, the garment comprises a man's brief, boxer-type undershorts, a woman's panty, panty hose, or a reusable diaper.

According to one preferred embodiment of the invention, the garment comprises a reusable and launderable diaper. The moisture management component is positioned in a crotch of the diaper, and includes a fabric comfort liner and a liquid impermeable, vapor permeable fabric layer. The fabric comfort liner resides between the moisture wicking panel and the skin of the wearer. The fabric comfort liner is constructed of moisture wicking fibers for residing in skin contact during garment wear and for wicking moisture away from the skin of the wearer. The liquid impermeable, vapor permeable fabric layer comprises a microfiber shield for providing a leak-proof barrier which prevents passage of liquid but permits dissipation of moisture in vapor form through the fabric.

Preferably, the moisture transport insert comprises a fabric panel having first and second end portions of gradually increasing width. The moisture transport insert extends generally from a front side of the garment through the crotch to a seat side of the garment.

According to one preferred embodiment of the invention, the moisture transport insert of the diaper comprises a fabric constructed substantially of moisture wicking fibers having a high surface area in relation to volume.

According to another preferred embodiment of the invention, the moisture transport insert of the diaper comprises an integrally knit hi-component fabric constructed of hydrophilic fibers on an inner face thereof for residing nearest the skin of the wearer, and moisture wicking fibers on an outer face thereof for residing away from the skin of the wearer.

According to yet another preferred embodiment of the invention, the moisture transport insert of the diaper comprises a fabric chemically treated for speeding the transport of moisture along the fibers of the moisture transport insert.

According to one preferred embodiment of the invention, the moisture wicking panel of the diaper comprises a fabric constructed of moisture wicking fibers having a high surface area in relation to volume.

According to another preferred embodiment of the invention, the moisture wicking panel of the diaper comprises an integrally knit hi-component fabric constructed of moisture wicking fibers on an inner fabric face thereof for residing nearest the skin of the wearer, and hydrophilic fibers on an obverse fabric face thereof for residing away from the skin of the wearer.

According to one preferred embodiment of the invention, the fabric comfort liner of the diaper comprises an integrally knit bi-component fabric constructed of moisture wicking fibers on an inner fabric face thereof for residing nearest the skin of the wearer, and hydrophilic fibers on an obverse fabric face thereof for residing away from the skin of the wearer.

According to one preferred embodiment of the invention, the garment is knitted of stretch yarns.

According to another preferred embodiment of the invention, the garment is knitted of non-stretch yarns.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
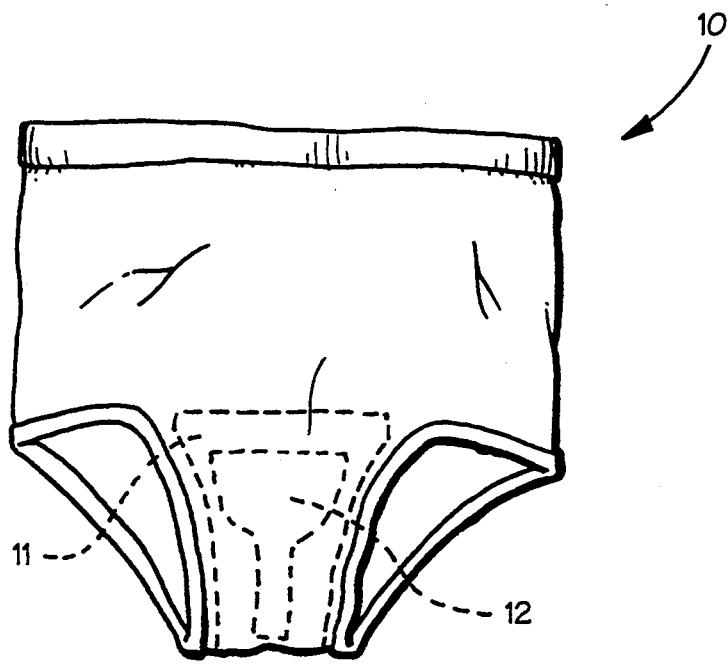
FIG. 1 is a front view of a man's brief showing the moisture management component in phantom according to one preferred embodiment of the present invention.

Referring now specifically to the drawings, a man's brief incorporating a moisture management component according to the present invention is illustrated in FIG. 1 and shown generally at reference numeral 10. The invention includes a moisture wicking panel 11 and moisture transport insert 12 located generally in the crotch area of a garment 10 for moving moisture upwardly and outwardly away from the skin of the wearer to drier areas of the garment 10 for evaporation. Except for the moisture management component, the garment 10 is constructed in a conventional manner to resemble a conventional garment in outward appearance.

Figure 2:
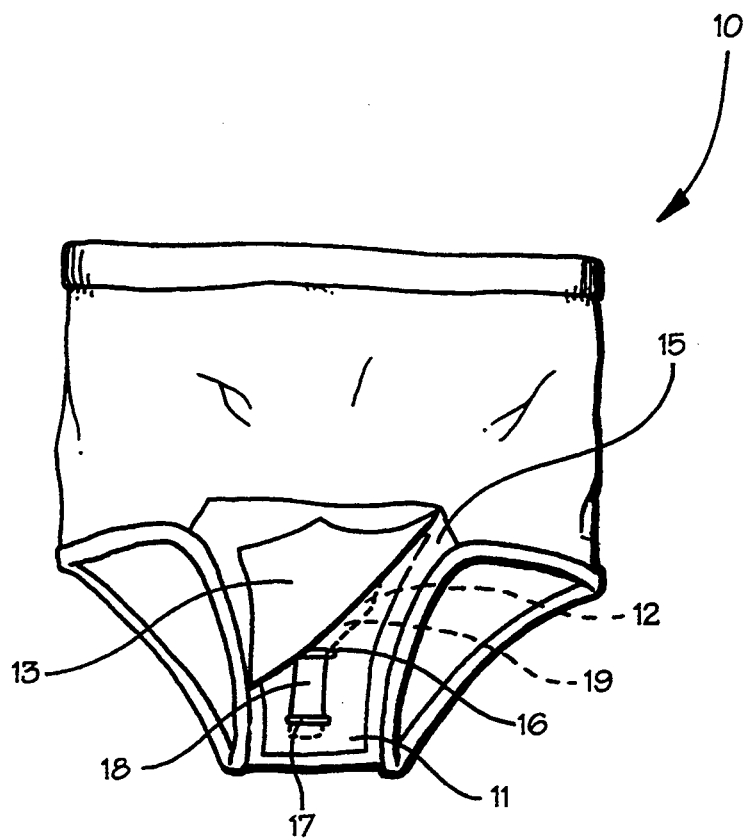
FIG. 2 is a view of the garment shown in FIG. 1 turned inside-out with fabric layers of the moisture management component peeled back.
Figure 3:
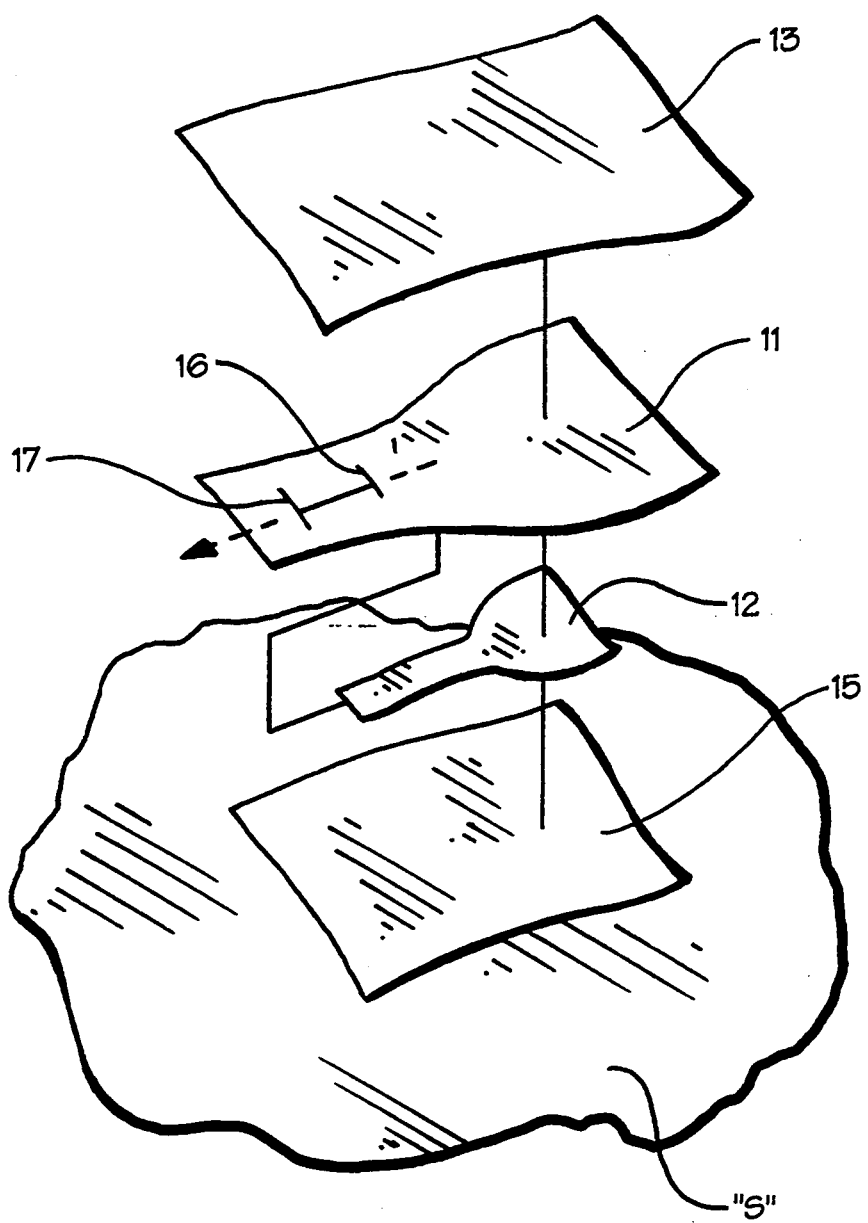
FIG. 3 is an exploded view of the moisture management component showing the various fabric layers according to a preferred embodiment of the invention.
Figure 11:
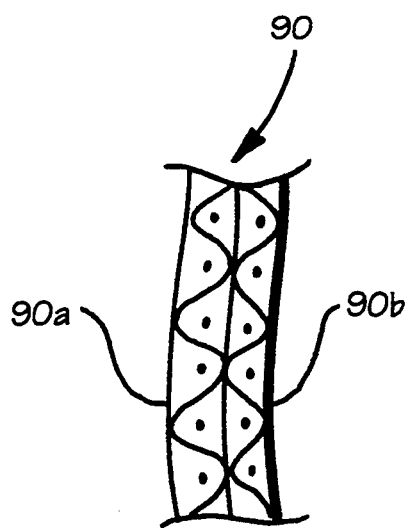
FIG. 11 is a cross-sectional view of a tri-component fabric according to another embodiment of the invention.

As shown in FIGS. 2 and 3, the garment 10 preferably includes a fabric comfort liner 13 for residing in skin contact during garment wear, and for providing added comfort to the wearer. The comfort liner 13 is preferably formed of an integrally knit bi-component fabric 90 constructed of moisture wicking fibers on an inner fabric face 90a, and hydrophilic fibers on an obverse fabric face 90b away from the skin (See FIG. 11). The moisture wicking fibers of the inner fabric face 90a are preferably hydrophobic polyester fibers for quickly moving moisture away from the skin and towards the outer layers of the garment 10. The "Coolmax" fibers manufactured by Dupont Corporation are preferably chosen for their exceptional ability to wick and move moisture. The hydrophilic fibers of the outer face 90b may consist of cotton, hydrophilic nylon, rayon, wool, blends of these fibers, or other similar hydrophilic fibers. In a second embodiment, the fabric comfort liner is constructed of a single-layer fabric formed substantially of hydrophobic polyester or polypropylene fibers having a high surface area in relation to volume. Although the comfort liner 13 is preferable, the garment 10 may be constructed without the liner while nevertheless achieving a similar moisture management effect.

Figure 4:
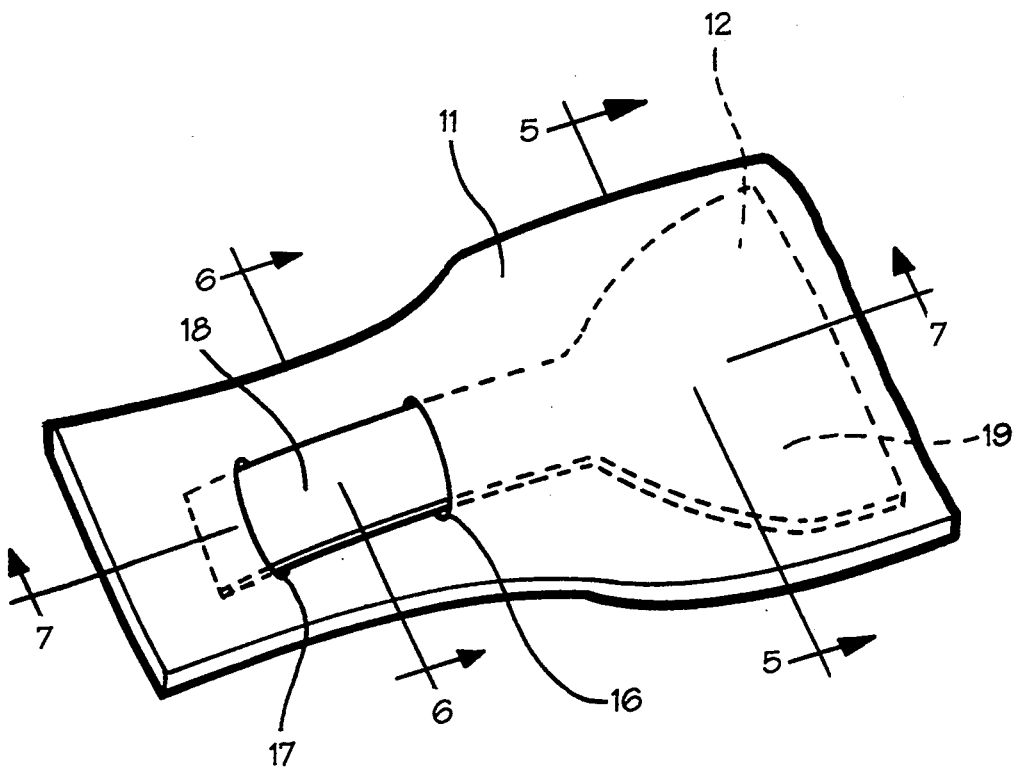
FIG. 4 is a perspective view of the moisture wicking panel and moisture transport insert showing the moisture transport insert extending through first and second openings.
Figure 5:
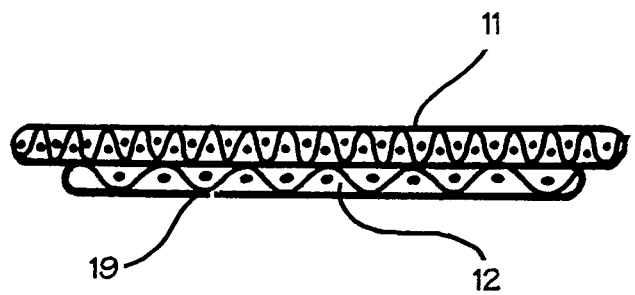
FIG. 5 is a cross-sectional view of the moisture wicking panel and moisture transport insert shown in FIG. 4 and taken substantially along the line 5—5.
Figure 6:
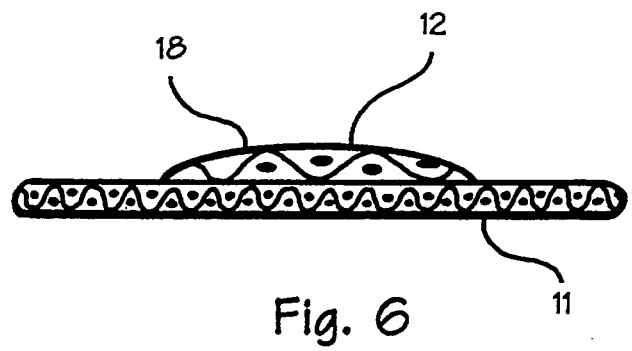
FIG. 6 is a cross-sectional view of the moisture wicking panel and moisture transport insert shown in FIG. 4 and taken substantially along the line 6—6.
Figures 7A, 7B:
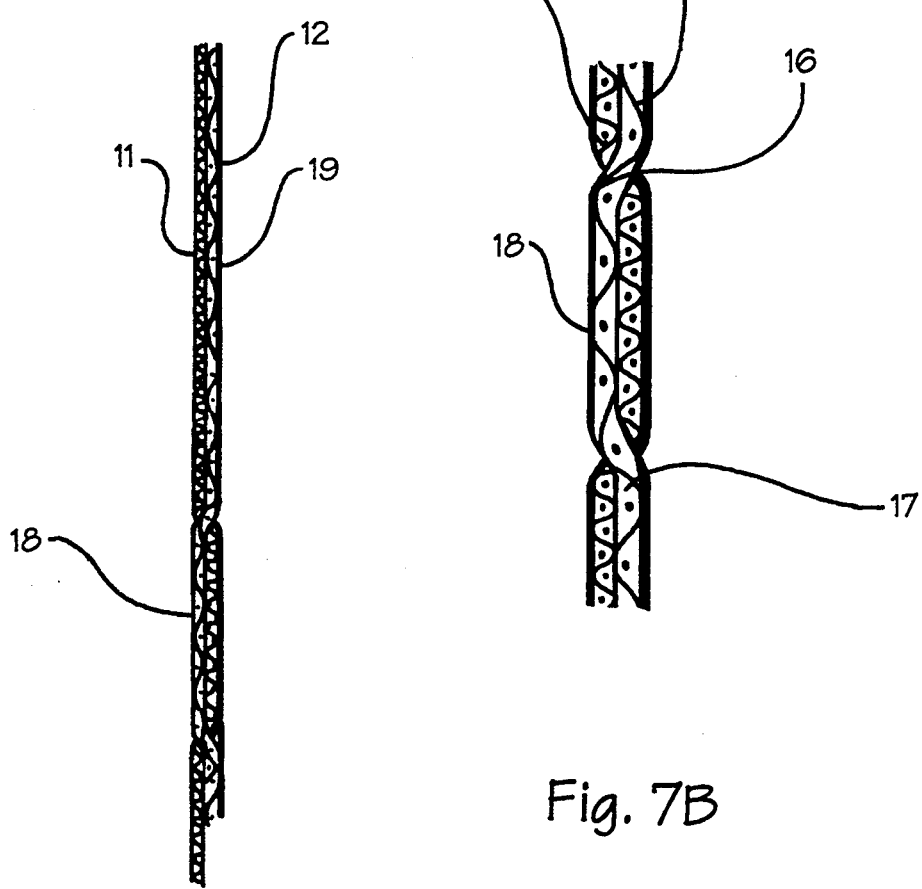
FIG. 7 is a cross-sectional view of the moisture wicking panel and moisture transport insert shown in FIG. 4 and taken substantially along the line 7—7.

The moisture wicking panel 11 and moisture transport insert 12 are located in the crotch area of the garment 10, adjacent to the fabric comfort liner 13. As shown in FIGS. 2, 3, and 4, the moisture wicking panel 11 has a first opening 16 formed therein through which the moisture transport insert 12 extends. The opening 16 defines first and second portions 18 and 19 (See FIG. 4) of the moisture transport insert 12 extending in respective opposite directions from the opening 16 and along opposite surfaces of the moisture wicking panel 11. The first portion 18 of the moisture transport insert 12 resides on a skin-side surface of the moisture wicking panel 11 in overlying relation to the moisture wicking panel 11. Preferably, the first portion 18 is located generally in the lower crotch area of the garment 10, and has a relatively small and narrow surface area. The narrow construction of the first portion 18 provides a more comfortable feel to the wearer in the lower crotch area of the garment 10 with a minimal amount of wetness maintained in the lower crotch area at any given time. The second portion 19 of the moisture transport insert 12 resides on the obverse side of the moisture wicking panel 11 away from the skin, and has a relatively large surface area. Preferably, the second portion 19 tapers outwardly, gradually increasing in width from the opening 16 and extending upwardly substantially to the top of the moisture wicking panel 11. FIGS. 5, 6, and 7 illustrate respective cross-sections of the moisture wicking panel 11 and moisture transport insert 12 taken substantially along lines 5—5, 6—6, and 7—7 of FIG. 4 to show the orientation of these elements with respect to the skin of the wearer.

Figure 8:
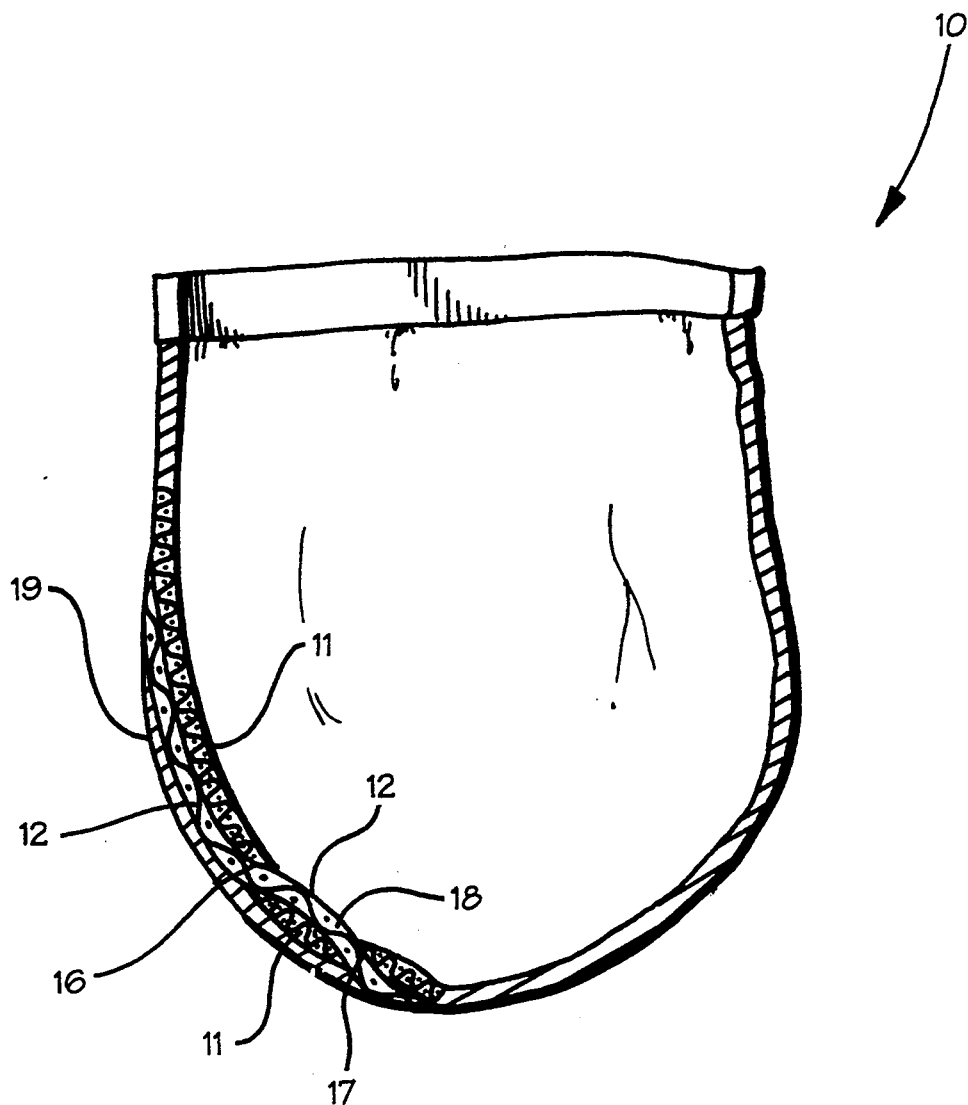
FIG. 8 is a cross-sectional side view of a man's brief showing the moisture wicking panel and moisture transport insert in exaggerated detail.

The smaller surface area of the first portion 18 acts to receive moisture wicked outwardly from the skin by the fabric comfort liner 13, and to quickly transport the moisture to the obverse side of the moisture wicking panel 11 away from the skin and along the fibers of the larger second portion 19. In the larger second portion 19, moisture is more readily dispersed and moved outwardly and upwardly towards the drier waist area of the garment 10. The position within the garment 10 of the first and second portions 18 and 19 of the moisture transport insert 12 and the moisture wicking panel 11 is best shown in FIGS. 1, 2, and 8.

The moisture wicking panel 11 may be provided with a second opening 17 located beneath the first opening 16 for receiving the free end of the moisture transport insert 12, as shown in FIGS. 2, 3, and 4.

The moisture wicking panel 11 and moisture transport insert 12 act to transport moisture upwardly away from the crotch area and outwardly away from the skin of the wearer by the movement of moisture along the longitudinal shafts of the fibers. The fiber composition of the moisture wicking panel 11 and moisture transport insert 12 is described below with reference to FIGS. 9, 10, and 11.

Figure 9:
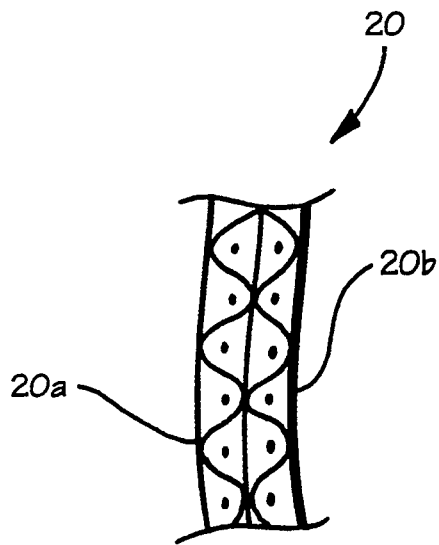
FIG. 9 is a cross-sectional view of a bi-component fabric of the moisture wicking panel according to one embodiment of the present invention.

Preferably, the moisture wicking panel 11 includes spandex fibers for providing stretch to the moisture wicking panel 11, and an integrally knit hi-component fabric 20. As shown in FIG. 9, the bi-component fabric 20 includes moisture wicking fibers on an inner fabric face 20a, and hydrophilic fibers on an obverse fabric face 20b. The moisture wicking fibers are preferably "Intera" nylon fibers processed by the Intera Corporation. These fibers are chemically processed to enhance the fibers' ability to quickly transport moisture. The hydrophilic fibers may include cotton, hydrophilic nylon, rayon, wool, blends of these fibers, or other similar hydrophilic fibers.

Alternately, the moisture wicking panel 11 may be constructed of a single-layer fabric formed of "Intera" nylon fibers, polypropylene, or "Coolmax" polyester fibers. The "Coolmax" fibers have a relatively high surface area in relation to volume, with channels running longitudinally along the shaft of the fiber to enhance the wicking or transport of moisture. Such fibers are designed specifically to move or wick moisture, and may be chemically processed to further enhance such ability.

Figure 10:
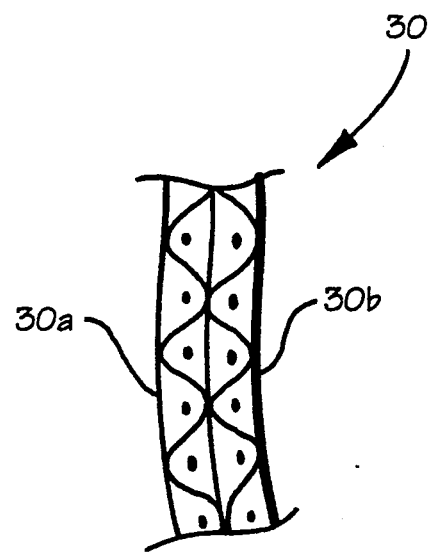
FIG. 10 is a cross-sectional view of a bi-component fabric of the moisture transport insert according to one embodiment of the present invention.

The moisture transport insert 12 is preferably constructed of an integrally knit bi-component fabric 30 formed of hydrophilic fibers on an inner fabric face 30a, and moisture wicking fibers on an obverse fabric face 30b (See FIG. 10). The hydrophilic fibers may consist of cotton, hydrophilic nylon, rayon, wool, blends of these fibers, or other similar hydrophilic fibers. The moisture wicking fibers are preferably a hydrophobic polyester, such as "Coolmax". In an alternate embodiment, the moisture transport insert is constructed of a single-layer fabric formed substantially of hydrophobic polyester fibers, such as "Coolmax" having a high surface area in relation to volume.

Figure 12:
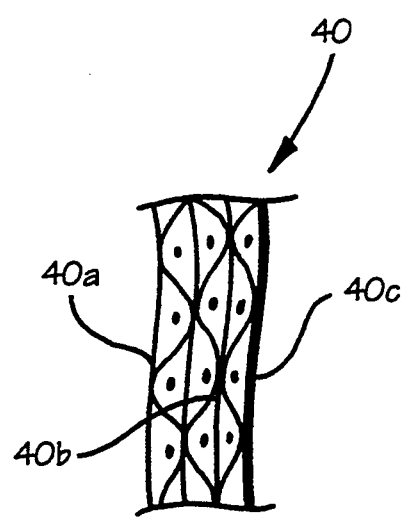
FIG. 12 is a cross-sectional view of a bi-component fabric of the fabric comfort liner according to one embodiment of the present invention.

According to yet another embodiment, the moisture wicking panel and/or the moisture transport insert may be formed of an integrally knit tri-component fabric 40 shown in FIG. 12. This fabric is constructed of hydrophobic polyester fibers on an innermost fabric face 40a next to the skin of the wearer, a first hydrophilic nylon component 40b residing adjacent to the hydrophobic polyester fibers and away from the skin of the wearer, and a second hydrophilic nylon component 40c residing adjacent to the first hydrophilic nylon component 40b and comprising an outermost fabric face of the tri-component fabric 40. Preferably, the second hydrophilic nylon component 40c has a brushed fabric face for enhancing the ability of the second nylon component 40c to disperse moisture moved outwardly from the first nylon component. The hydrophilic nylon may be the "Hydrofil" fibers manufactured by Allied Fibers Corporation, or "Intera" nylon.

According to another preferred embodiment of the invention, the garment further includes a liquid impermeable, vapor permeable microfiber fabric layer comprising a microfiber shield 15 shown in FIGS. 2 and 3. The microfiber shield 15 resides adjacent to the shell fabric "S" of the garment, and is preferably constructed of nylon or polyester microfibers. Although the microfiber shield 15 is liquid impervious, it permits the dissipation of moisture from the garment 10 in vapor form. Additionally, the shield 15 does not produce a rustling or crinkling noise when worn. This fabric is particularly desirable in garments for individuals with mild incontinence.

Figure 13:
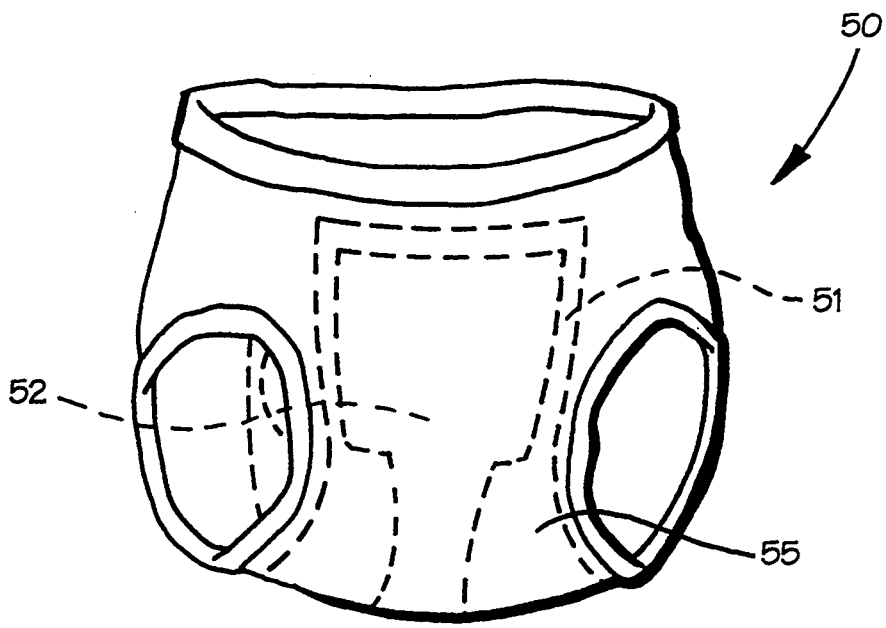
FIG. 13 is a perspective view of a baby's diaper showing the moisture management component in phantom.
Figure 14:
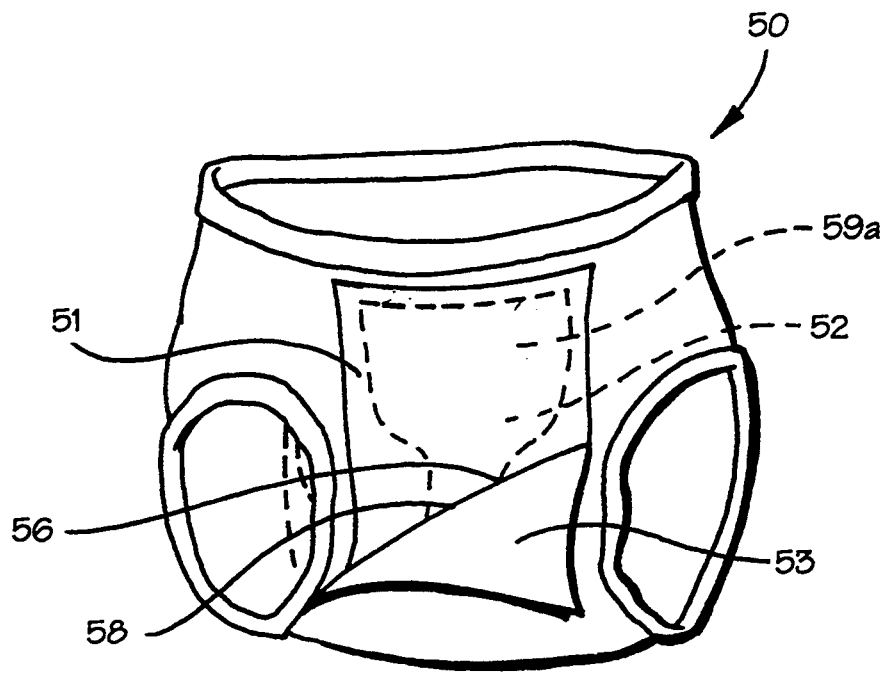
FIG. 14 is a view of the diaper shown in FIG. 13 turned inside-out with the various fabric layers of the moisture management component peeled back.

A reusable and launderable baby diaper 50 incorporating the moisture management component of the present invention is shown in FIGS. 13 and 14. The diaper 50 preferably includes both the fabric comfort liner 53 and outer microfiber shield 55 described above. The fiber composition of these layers is equivalent to that described above with reference to the man's brief illustrated in FIGS. 1, 2, and 8.

Figure 15:
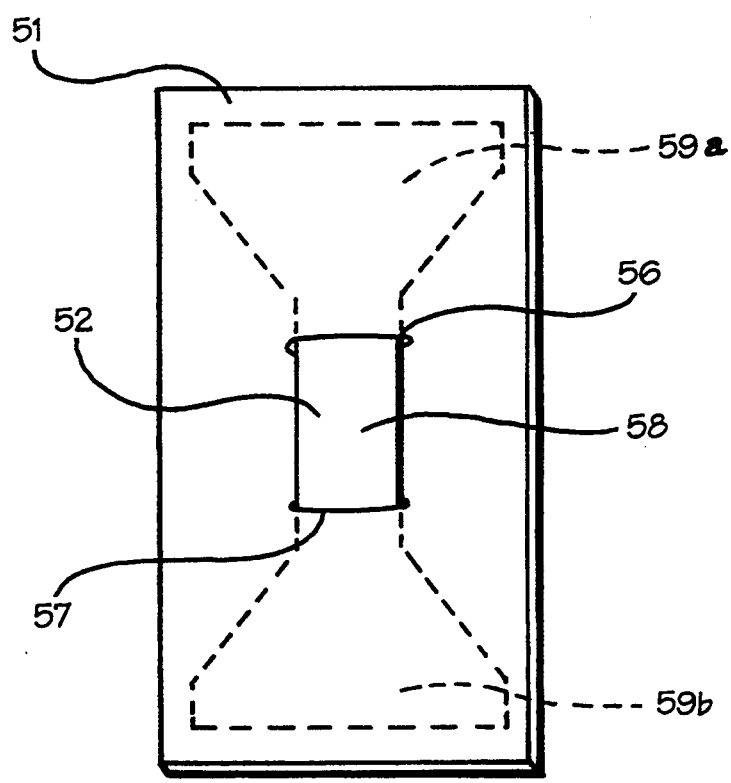
FIG. 15 is a perspective view of the moisture wicking panel and moisture transport insert according to another embodiment of the invention for particular use in a diaper and panty hose.

The diaper 50 further includes a similar moisture wicking panel 51 and moisture transport insert 52 as described above and shown in FIG. 15. The moisture wicking panel 51 and moisture transport insert 52 are located on a front side of the diaper 50 and extend through the crotch area to a seat side of the diaper 50. Preferably, the moisture wicking panel 51 and moisture transport insert 52 extend substantially to the front and back waist areas of the diaper 50, as shown in FIGS. 13 and 14. The fiber composition of the moisture wicking panel 51 and moisture transport insert 52 is equivalent to that described above with reference to the man's brief 10.

The moisture wicking panel has first and second openings 56 and 57 formed therein through which the moisture transport insert 52 extends. The openings 56 and 57 define three portions of the moisture transport insert 52. The first portion 58 of the moisture transport insert 52 resides on a skin-side surface of the moisture wicking panel 51 in overlying relation to the moisture wicking panel 51. Preferably, the first portion 58 is located generally in the lower crotch area of the diaper 50, and has a relatively small and narrow surface area. The relatively narrow construction of the first portion 58 provides a more comfortable fit in the crotch area of the diaper 50, while reducing the amount of wetness retained in the crotch area at any given time.

The second and third portions 59a and 59b of the moisture transport insert 52 reside on the obverse side of the moisture wicking panel 51 away from the skin of the baby. These portions 59a–b have a relatively large and wide surface area tapering outwardly in respective opposite directions and gradually increasing from the relatively narrow first portion 58 of the moisture transport insert 52. Preferably, the second portion 59a extends upwardly substantially to the top of the moisture wicking panel 51 on the front side of the diaper 50. Likewise, the third portion 59b extends upwardly substantially to the top of the moisture wicking panel 51 on the seat side of the diaper 50.

The smaller and narrower surface area of the first portion 58 acts to receive moisture wicked outwardly from the skin by the fabric comfort liner 53, and to quickly transport the moisture to the obverse side of the moisture wicking panel 51 away from the skin and along the fibers of the larger second and third portions 59a-b. In the larger portions 59a-b, moisture is more readily dispersed and moved outwardly and upwardly towards the drier waist area on the front and seat sides of the diaper 50.

Preferably, the diaper 50 further includes one or more layers of cotton or other hydrophilic fibers (not shown) positioned adjacent to the moisture wicking panel 51. The moisture transport insert 52 extends through each cotton layer such that the first portion 58 of the moisture transport insert 52 resides adjacent to the fabric comfort layer 53. This provides added comfort to the wearer, while not impeding the ability of the moisture transport insert 52 to receive and move moisture away from the baby's skin.

According to an alternate embodiment (not shown), the moisture transport insert 52 of the diaper comprises a rectangular panel extending generally from a front side of the diaper 50 through the crotch to a seat side of the diaper 50.

The moisture management component of the present invention may be incorporated in other garments such as a woman's panty, panty hose, or boxer-type undershorts. The fiber composition and orientation of the various layers of the moisture management component in the respective garments is equivalent to that described above with reference to the man's brief 10 and diaper 50.

Figure 16:
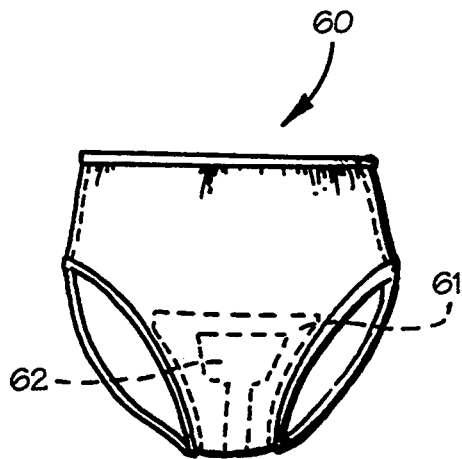
FIG. 16 is a perspective view of a woman's panty showing the moisture management component in phantom.

The woman's panty 60 is illustrated in FIG. 16. For women with mild incontinence, the panty would include the microfiber shield (not shown) positioned between the moisture wicking panel 61 and the outer shell fabric of the garment. Like the previously described garments, the panty 60 includes a moisture transport insert 62 passing through an opening formed in the moisture wicking panel for quickly and directly moving moisture from the skin of the wearer to the outer layers of the garment.

Figure 17:
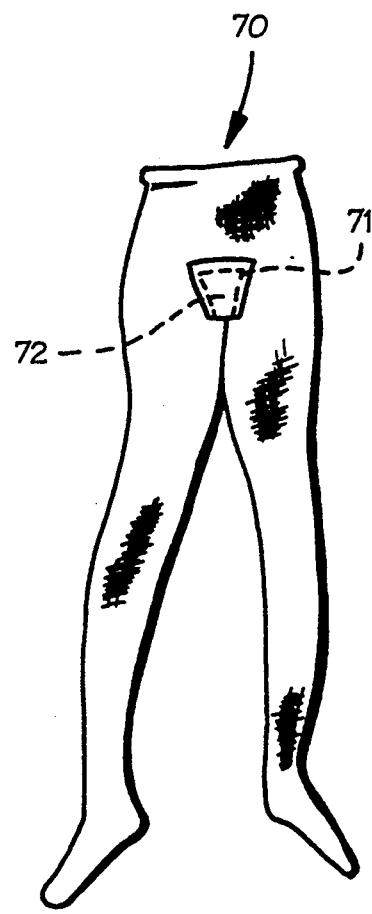
FIG. 17 is a perspective view of a pair of panty hose showing the moisture management component in phantom.

The pair of panty hose 70 is illustrated in FIG. 17. Preferably, the panty hose 70 does not include the microfiber shield. The moisture wicking panel 71 and moisture transport insert 72 are constructed as described above, and may be shaped as shown in FIG. 15. Preferably, the moisture wicking panel 71 and moisture transport insert 72 extend from the upper crotch area of the panty hose 70 to the lower crotch area.

Figure 18:
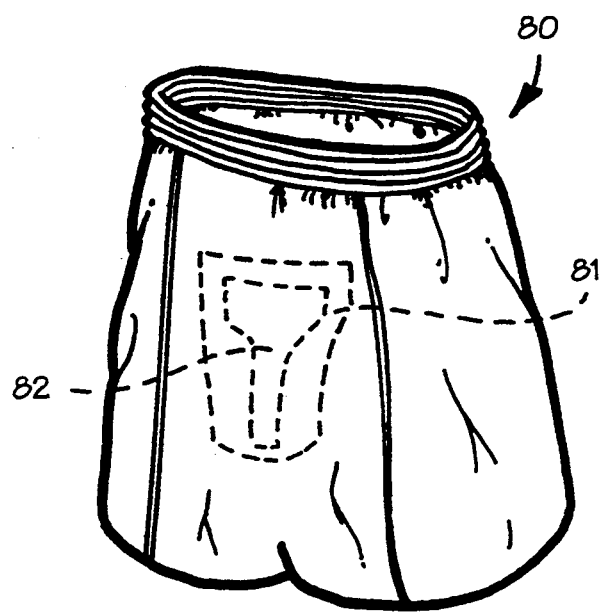
FIG. 18 is a perspective view of boxer-type undershorts showing the moisture management component in phantom.

The boxer-type undershort 80 is illustrated in FIG. 18. Like the panty 60, this garment would include a microfiber shield (not shown) positioned between the moisture wicking panel 81 and the outer shell fabric for men with mild incontinence. The moisture wicking panel 81 and moisture transport insert 82 are positioned in the crotch area of the garment as previously described.

Launderable and reusable garments incorporating a moisture management component according to the present invention are described above. Various details of the invention may be changed without departing from its scope. Furthermore, the foregoing description of the preferred embodiment of the invention is provided for the purpose of illustration only and not for the purpose of limitation-the invention being defined by the claims.

We claim:

1. In a garment, the improvement comprising a moisture management component for moving moisture away from the skin of a wearer, said moisture management component including:
   (a) a first fabric comprising a moisture wicking panel carried by said garment for moving moisture away from the skin, and having a skin-side surface and an obverse surface; said moisture wicking panel defining an opening therethrough from said skin-side surface to said obverse surface; and
   (b) a second fabric comprising a moisture transport insert extending through the opening in said moisture wicking panel, and having:
      (1) a first portion positioned in overlying relation on the skin-side surface of the moisture wicking panel for receiving moisture from the skin and from the moisture wicking panel; and
      (2) a second portion positioned in overlying relation on the obverse surface of said moisture wicking panel for receiving moisture from the first portion of the moisture transport insert and for transporting said moisture through the opening to the obverse face of the moisture wicking panel for dispersal throughout the obverse face.

2. A garment according to claim 1, wherein the first portion of said moisture transport insert resides generally in a lower crotch area of said garment and is relatively narrow with a relatively small surface area; and the second portion of said moisture transport insert resides generally in an upper crotch area of said garment and is relatively wide with a relatively large surface area, said second portion providing greater moisture absorption capacity in the upper crotch area of the garment to promote the transport of moisture upwardly towards a drier area of the garment where moisture can more easily be dispersed.

3. A garment according to claim 2, wherein the width of said moisture transport insert tapers from the relatively wide second portion towards the relatively narrow first portion.

4. A garment according to claim 2, wherein said moisture wicking panel defines a second opening therethrough located in spaced-apart relation to said first opening for receiving a free end of the relatively narrow first portion of said moisture transport insert through said moisture wicking panel from the skin-side surface of said moisture wicking panel to the obverse surface of said moisture wicking panel.

5. A garment according to claim 1 or 2, wherein said moisture wicking panel comprises a fabric constructed of moisture wicking fibers having a high surface area in relation to their volume.

6. A garment according to claim 1 or 2, wherein said moisture wicking panel comprises an integrally knit bi-component fabric constructed of moisture wicking fibers on an inner fabric face thereof for residing nearest the skin of the wearer, and hydrophilic fibers on an obverse fabric face thereof for residing away from the skin of the wearer.

7. A garment according to claim 1 or 2, wherein said moisture transport insert comprises a fabric constructed substantially of moisture wicking fibers having a high surface area in relation to their volume.

8. A garment according to claim 1 or 2, wherein said moisture transport insert comprises an integrally knit bi-component fabric constructed of hydrophilic fibers on an inner fabric face thereof for residing nearest the skin of the wearer, and moisture wicking fibers on an obverse fabric face thereof for residing away from the skin of the wearer.

9. A garment according to claim 1 or 2, wherein said moisture transport insert comprises a fabric chemically processed for speeding the movement of moisture along the fibers of said moisture transport insert.

10. A garment according to claim 1 or 2, wherein said moisture management component includes a fabric comfort liner constructed of moisture wicking fibers for residing between the moisture wicking panel and the skin of the wearer to wick moisture away from the skin of the wearer.

11. A garment according to claim 1 or 2, wherein said moisture management component includes a fabric comfort liner comprising an integrally knit bi-component fabric constructed of moisture wicking fibers on an inner fabric face thereof for residing nearest the skin of the wearer, and hydrophilic fibers on an obverse fabric face thereof for residing away from the skin of the wearer.

12. A garment according to claim 1 or 2, wherein said moisture management component further includes a liquid impermeable, vapor permeable microfiber fabric layer comprising a microfiber shield for providing a leak-proof barrier which prevents passage of liquid but permits dissipation of moisture in vapor form through the fabric.

13. A garment according to claim 1 or 2, wherein the garment comprises a man's brief, boxer-type undershorts, a woman's panty, panty hose, or a reusable diaper.

14. A garment according to claim 1, wherein said garment comprises a reusable and launderable diaper, and said moisture management component being positioned in a crotch area of the diaper, and comprising:
   (a) a fabric comfort liner for residing between the moisture wicking panel and the skin of the wearer; said fabric comfort liner constructed of moisture wicking fibers for residing in skin contact during garment wear and for wicking moisture away from the skin of the wearer; and
   (b) a liquid impermeable, vapor permeable microfiber fabric layer comprising a microfiber shield for providing a leak-proof barrier which prevents passage of liquid but permits dissipation of moisture in vapor form through the fabric.

15. A garment according to claim 1 or 14, wherein said moisture transport insert comprises a fabric panel having first and second end portions of gradually increasing width, said moisture transport insert extending generally from a front side of said garment through the crotch to a seat side of said garment.

16. A garment according to claim 14, wherein said moisture transport insert comprises a fabric constructed substantially of moisture wicking fibers having a high surface area in relation to their volume.

17. A garment according to claim 14, wherein said moisture transport insert comprises an integrally knit bi-component fabric constructed of hydrophilic fibers on an inner face thereof for residing nearest the skin of the wearer, and moisture wicking fibers on an outer face thereof for residing away from the skin of the wearer.

18. A garment according to claim 14, wherein said moisture transport insert comprises a fabric chemically processed for speeding the transport of moisture along the fibers of said moisture transport insert.

19. A garment according to claim 14, wherein said moisture wicking panel comprises a fabric constructed of moisture wicking fibers having a high surface area in relation to their volume.

20. A garment according to claim 14, wherein said moisture wicking panel comprises an integrally knit bi-component fabric constructed of moisture wicking fibers on an inner fabric face thereof for residing nearest the skin of the wearer, and hydrophilic fibers on an obverse fabric face thereof for residing away from the skin of the wearer.

21. A garment according to claim 14, wherein said fabric comfort liner comprises an integrally knit bi-component fabric constructed of moisture wicking fibers on an inner fabric face thereof for residing nearest the skin of the wearer, and hydrophilic fibers on an obverse fabric face thereof for residing away from the skin of the wearer.

22. A garment according to claim 1 or 14, wherein said garment is constructed of a fabric knitted of stretch yarns.

23. A garment according to claim 1 or 14, wherein said garment is constructed of a fabric knitted of non-stretch yarns.

24. A moisture management component for use in a garment for moving moisture away from the skin of a wearer, said moisture management component including:
   (a) a first fabric comprising a moisture wicking panel carried by said garment for moving moisture away from the skin, and having a skin-side surface and an obverse surface; said moisture wicking panel defining an opening therethrough from said skin-side surface to said obverse surface; and
   (b) a second fabric comprising a moisture transport insert extending through the opening in said moisture wicking panel, and having:
      (1) a first portion positioned in overlying relation on the skin-side surface of the moisture wicking panel for receiving moisture from the skin and from the moisture wicking panel; and
      (2) a second portion positioned in overlying relation on the obverse surface of said moisture wicking panel for receiving moisture from the first portion of the moisture transport insert and for transporting said moisture through the opening to the obverse face of the moisture wicking panel for dispersal throughout the obverse face.

* * * * *